United States Patent [19]

Nelson

[11] 4,385,627
[45] May 31, 1983

[54] HEAD STABILIZER ACCESSORY

[76] Inventor: Gayle V. Nelson, 101 S. Cleveland, Sioux Falls, S. Dak. 57103

[21] Appl. No.: 173,372

[22] Filed: Jul. 29, 1980

[51] Int. Cl.³ .............................................. A61F 5/01
[52] U.S. Cl. ................................................. 128/76 R
[58] Field of Search .................. 128/38, 39, 40, 44, 128/64, 66, 75, 76, 84, 92 R, 92 CA, 133, 134, 163; 272/94, 95, 96, 119; 250/320

[56] References Cited

U.S. PATENT DOCUMENTS

| 2,088,207 | 7/1937  | Kaiser     | 128/DIG. 23 |
| 2,225,896 | 12/1940 | Belknap    | 128/133     |
| 3,224,439 | 12/1965 | Blair      | 128/DIG. 23 |
| 3,397,688 | 8/1968  | Gottfried  | 128/76 R    |
| 3,548,816 | 12/1970 | Bond       | 128/76 R X  |
| 3,643,996 | 2/1972  | Carnahan   | 128/75 X    |
| 3,936,641 | 2/1976  | Heimur     | 250/456     |
| 4,153,841 | 5/1979  | Kok        | 250/456     |
| 4,182,322 | 1/1980  | Miller     | 128/76 R X  |
| 4,267,830 | 5/1981  | Vick       | 128/134     |

FOREIGN PATENT DOCUMENTS 420868 11/1925 Fed. Rep. of Germany .

Primary Examiner—Richard J. Apley
Assistant Examiner—R. C. Moy

[57] ABSTRACT

A head stabilizer accessory for use with head immobilizing devices containing a pair of horizontally adjustable, vertical elements for positioning the head therebetween, said accessory comprising two separate, flexible members each having at one end thereof means for securing same to respective ones of said vertical elements, said flexible members being of a length enabling the members, after securing same to said vertical elements, to be wrapped about and fastened behind said head and including means near the ends of each of said members opposite the ends containing the securing means for fastening said members together.

6 Claims, 5 Drawing Figures

HEAD STABILIZER ACCESSORY

BACKGROUND OF THE INVENTION

This invention relates to a head stabilizer accessory for use with head immobilizing devices such as head immobilizing devices used with panoramic x-ray machines.

There are numerous instances in the health care field wherein it is necessary to "stabilize" the patient's head during treatment. Consequently, a variety of devices for immobilizing the human head have been developed and illustrative of such devices are those used with panoramic x-ray machines. Panoramic x-ray equipment operates to arcuately scan a dental patient's oral structures with a narrow x-ray beam directed through the mouth region of the head toward a film carrier on the opposite side of the patient's head. Although the x-ray equipment traverses an arcuate path around the patient's head, the beam is discontinuous during traverse so as not to irradiate the spine. Also the beam direction shifts relative to the film carrier during a traverse so that a full mouth oral structure image is obtained on a rectangular film supported in the carrier. It is important that the patient's head not move during the scan period for any movement during such period distorts at least part of the x-ray image.

The head immobilizing device described, for example, in U.S. Pat. Nos. 3,521,057 and 3,936,641 exemplify commercially successful units of this type. These immobilizing devices are characterized by two horizontally adjustable vertical or upright elements for positioning the head therebetween. Ordinarily there is also a chin rest which may or may not be adjustable. While this type of head immobilizer of the prior art restricts head movement downward and side-to side it does not prevent upward or backward movement of the head. The latter shortcoming of the device presents no problem with the "normal" patient who has the ability to hold his head absolutely still for 10 to 15 continuous seconds but this inability to prevent upward or backward movement of the head has been found to be a frequent cause of malpositioning when the patient is a child or handicapped person.

SUMMARY OF THE INVENTION

The present invention relates to an accessory for use with immobilizing devices containing a pair of horizontally adjustable, vertical or upright elements for positioning the head therebetween which accessory prevents upward or backward movement of the head. The head stabilizer accessory comprises two separate, flexible members each having at one end thereof means for securing same to respective ones of said vertical elements, said flexible members being of a length enabling the members, after securing same to said vertical elements, to be wrapped about and fastened behind said head and including means near the ends of each of said members opposite the ends containing the securing means for fastening said members together.

In a preferred embodiment the means for securing the flexible members to the vertical elements comprise a vertical sleeve at one end of each flexible member, which sleeves receive the respective vertical elements.

In another aspect, the head stabilizer accessory includes a chin strap means.

BRIEF DESCRIPTION OF THE DISCLOSURE

DESCRIPTION OF PREFERRED EMBODIMENT

While the following description of the head stabilizer accessory of the invention is made in reference to a head immobilizing device for use in panoramic x-ray machines, it should be understood that the invention can be employed with any head immobilizing device that contains a pair of horizontally adjustable, vertical or upright elements for positioning a head therebetween.

Figure 1:
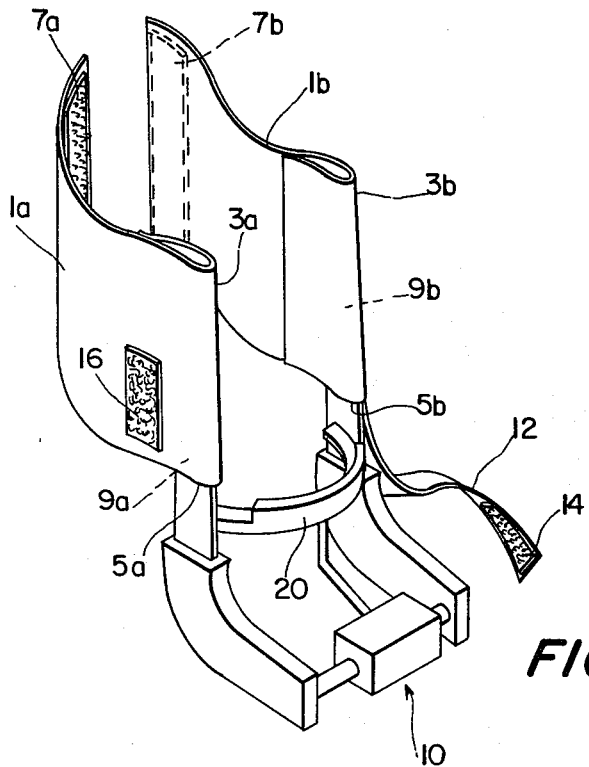
FIG. 1 is a perspective view of the head stabilizer accessory in combination with a head immobilizing device for panoramic x-ray apparatus.
Figure 4:
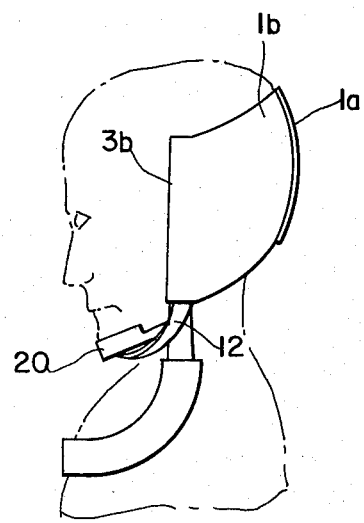
FIG. 4 is a side view of the head stabilizing accessory/head immobilizing device in relation to a positioned patient's head.

Referring to the figures the head stabilizing accessory is comprised of two flexible members 1a and 1b each having at the outer ends sleeves 3a and 3b. The openings for sleeve 3a and sleeve 3b are at the bottom of each flexible member and are indicated by members 5a and 5b. The flexible members can be constructed of any suitable flat flexible material, for example, textile material such as cloth, canvas, etc., leather, plastic sheet materials and the like. Preferably the flexible material is made of a durable canvas. Advantageously the flexible members 1a and 1b taper upwardly from said sleeve-bearing ends so as to conform to cover substantially the entire back of the head. The feature is best shown in FIG. 1 and FIG. 4.

Figure 2:
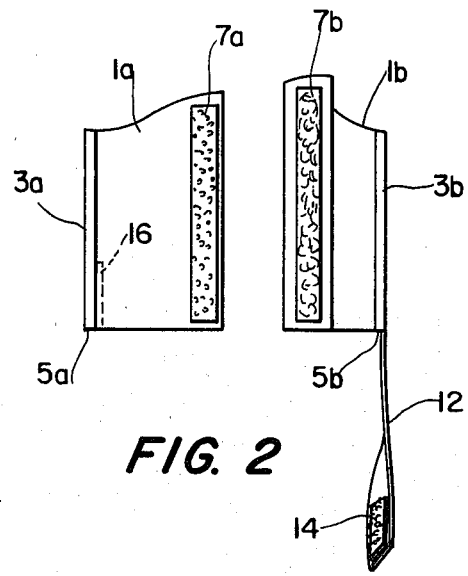
FIG. 2 is a plan view of the flexible members of the head stabilizing accessory including a chin strap.
Figure 3:
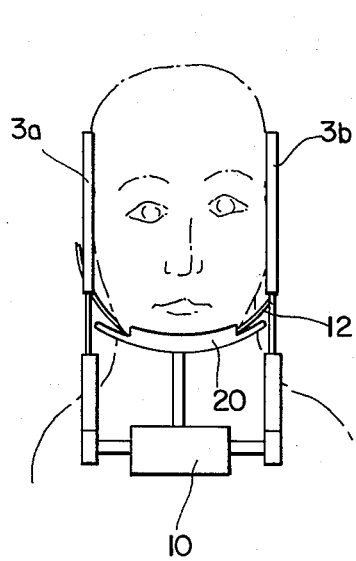
FIG. 3 is a front view of the head stabilizing accessory/head immobilizing device in relation to a positioned patient's head.

The ends of the flexible members opposite the sleeves 3a and 3b are provided with fastening means comprised of two strips, 7a and 7b. Strip 7a is securely attached to the inner surface of flexible member 1a and has affixed thereto small flexible hooks (e.g. made of plastic). Thus trip 7a constitutes a receiving means. Strip 7b is securely attached to the outer surface of flexible member 1b as shown in phantom in FIG. 1 and is comprised of a receiving matting formed of a plurality of small closed loops of thread. As can be seen best from FIG. 2, and FIG. 4 the flexible members are of a length such that when the vertical or upright elements 9a and 9b of head immobilizing device are inserted in sleeves 3a and 3b, respectively, the flexible members wrap tightly around the back of the patients head and overlap so that the gripping means, i.e. strip 7a, coincides with the receiving means, strip 7b for fastening the members together.

It is preferred that the head stabilizing accessory of the invention include a chin strap means 12. Chin strap means 12 can be fastened to the flexible members 1a and 1b in any suitable fashion, for instance, by the use of gripping means and receiving means such as described with reference to strips 7a and 7b above. Alternatively, one end of the chin strap means can be permanently fastened to one of the flexible members as shown in FIG. 1 while at the other end thereof is attached a strip 14 as a gripping means. Strip 14 has affixed to it a plurality of hooks for engagement with a receiving means in the form of a strip 16 secured to the outer surface of flexible member 1a as shown in phantom in FIG. 1.

Figure 5:
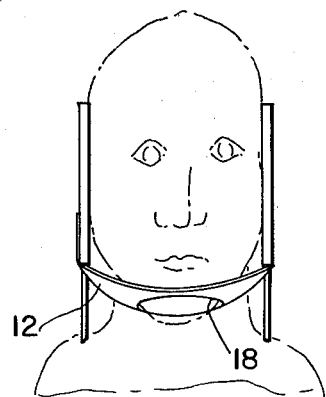
FIG. 5 is a front view of the head stabilizing accessory/head immobilizing device in relation to a positioned patient's head including a modified chin strap.

FIG. 5 shows a chin strip 12 modified to contain an opening 18 for accomodating the chin rest 20 of the head immobilizing device 10. The ends of the modified chin strap are secured to the flexible members by gripping means and receiving means (neither of which is shown) similar to strips 14 and 15, respectively, described above.

In operation, vertical elements 9a and 9b are inserted in sleeves 3a and 3b respectively. The vertical elements 9a and 9b are spaced apart and the seated patient's head is moved in between. Chin rest 20 of the head immobilizing device 20 is then adjusted until the patient's chin rests comfortably thereon. Vertical elements 9a and 9b are then moved towards one another until they engage the sides of the patients head and set at this position. The particular mechanism or means by which this is accomplished is not essential to the invention and therefore its description is not deemed necessary. Suffice it to say the specific head immobilizing devices suitable for use with the present invention have been described in detail in, for instance, U.S. Pat. No. 3,521,057 of A. F. Morlan and U.S. Pat. No. 3,936,641 to Karl Heimur, each of which is hereby incorporated by reference.

After the patient's head and chin have been positioned as described above, flexible members 1a and 1b are wrapped tightly about and behind the head so that flexible member 1b overlaps flexible member 1a at the back of the head. Overlapping portion of flexible member 1b will contain strip 7b (the gripping means), which ends up overlying strip 7a (the receiving means), for easy fastening. Chin strap 12 is then brought under the patient's chin and chin rest 20 and fastened by means of strip 14 attaching to strip 16.

Although this invention has been described with reference to particular embodiments, it will be understood to those skilled in the art that this invention is also capable of alternate embodiments within the spirit and scope of the claims. For instance, the flexible members can be attached to the vertical or upright elements of the head immobilizing devices by fastening means other than the described sleeves. Snaps, for example, are illustrative of one such alternative means. Thus, vertical elements can be provided with the male portion of a plurality of said snaps and the flexible member with the female portion or vice versa. Also, the invention is also applicable to head immobilizing devices of the type having the horizontally-adjustable, vertical elements for positioning the head therebetween originating from above the top of the head rather than below. The head stabilizer accessory of the invention can be secured to the adjustable elements of this alternate device in similar manner and will contact the sides of the head at approximately the same position when fastened behind the head. Other alternative means will be readily apparent to those of ordinary skill in the art.

It is claimed:

1. In combination, a head immobilizing device containing a pair of horizontally adjustable, vertical elements for positioning the head therebetween and a head stabilizer accessory comprising two separate, flexible members each having at one end thereof means for securing same to respective ones of said vertical elements, said flexible members being of a length enabling the members, after securing same to said vertical elements, to be wrapped about and fastened behind said head and including means near the ends of each of said members opposite the ends containing the securing means for fastening said members together, and said flexible members tapering upwardly from said ends bearing the securing means so as to conform to and cover substantially the entire back of the head.

2. The combination of claim 1 including a chin strap means one end of which is removably attachable to one of said flexible members and means for fastening the other end of said chin strap to the other flexible member.

3. The combination of claim 2 wherein the chin strap is fastened to flexible members by means comprising in combination a receiver means provided with a plurality of flexible loops affixed to the outer surface of each of the flexible members and a gripping means provided with a plurality of hooks affixed to the inner surface of each end of said chin strap.

4. The combination of claim 1 including a chin strap means wherein one end of the strap is permanently secured to the base of one of said members and means for fastening the other end of said chin strap to the opposite flexible member.

5. The combination of claim 1 wherein the fastening means for the flexible members comprises in combination a receiver means provided with a plurality of flexible loops affixed to outer or inner surface of one of the flexible members and a gripping means provided with a plurality of hooks affixed to the opposite surface of the other flexible member.

6. In combination, a head immobilizing device containing a pair of horizontally adjustable, vertical elements for positioning the head therebetween and a head stabilizer accessory comprising two separate, flexible members each having at one end thereof a vertical sleeve for receipt of respective ones of said vertical elements, said flexible members having a top edge and a bottom edge, said top edge tapering upwardly from substantially the top of the vertical element to the top rear portion of the head and said bottom edge extending rearwardly from the vertical element along the base of the head and said flexible members being of a length enabling the members after insertion of said vertical elements into the respective sleeves to be wrapped about the head so as to overlap at the rear of the head and means along said overlapping portions for fastening said members together.

* * * * *